US009789275B2

(12) United States Patent
Iyer et al.

(10) Patent No.: US 9,789,275 B2
(45) Date of Patent: Oct. 17, 2017

(54) SYSTEM AND METHOD FOR ENTRAINING THE BREATHING OF A SUBJECT

(75) Inventors: Vijay Kumar Iyer, Murrysville, PA (US); Michael Edward Colbaugh, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 1130 days.

(21) Appl. No.: 13/377,184

(22) PCT Filed: Jun. 16, 2010

(86) PCT No.: PCT/IB2010/052713
§ 371 (c)(1),
(2), (4) Date: Dec. 9, 2011

(87) PCT Pub. No.: WO2011/004274
PCT Pub. Date: Jan. 13, 2011

(65) Prior Publication Data
US 2012/0085347 A1    Apr. 12, 2012

Related U.S. Application Data

(60) Provisional application No. 61/224,113, filed on Jul. 9, 2009.

(51) Int. Cl.
*A61M 21/00* (2006.01)
*A61M 16/06* (2006.01)
(Continued)

(52) U.S. Cl.
CPC ........ *A61M 21/00* (2013.01); *A61M 16/0666* (2013.01); *A61M 16/0866* (2014.02);
(Continued)

(58) Field of Classification Search
CPC .............. A61M 21/00; A61M 16/0866; A61M 16/0666; A61M 2021/0088;
(Continued)

(56) References Cited

U.S. PATENT DOCUMENTS 3,511,228 A    5/1970 Lundgren et al.
3,710,780 A    1/1973 Milch
(Continued)

FOREIGN PATENT DOCUMENTS

JP    2009082175 A    4/2009
RU    2164805 C1    4/2001
(Continued)

OTHER PUBLICATIONS

Wikipedia "Servomotor" article from http://en.wikipedia.org/w/index.php?title=Special:Book&bookcmd=download&collection_id=0174f25d71d7c59ca34c23510ac32e7088b2fa1e&writer=rdf2latex&return_to=Servomotor.*

*Primary Examiner* — Kathryn E Ditmer (57) ABSTRACT

A respiration appliance (10) is configured to entrain the breathing of the subject. The breathing of the subject is entrained to modulate the autonomic nervous system of the subject to decrease sympathetic nerve activity and/or to reduce sympathetic/parasympathetic balance in order to provide relaxation to the subject. The respiration appliance (10) restricts the exhalation of the subject, while permitting substantially unencumbered inhalation, to impact the breathing of the subject in a manner that enhances relaxation.

15 Claims, 4 Drawing Sheets

(51) Int. Cl.
*A63B 23/18* (2006.01)
*A61M 16/08* (2006.01)
*A61M 16/00* (2006.01)
*A63B 21/008* (2006.01)
*A63B 24/00* (2006.01)

(52) U.S. Cl.
CPC ......... *A63B 23/18* (2013.01); *A61M 16/0683* (2013.01); *A61M 2016/0033* (2013.01); *A61M 2021/0088* (2013.01); *A61M 2205/3553* (2013.01); *A61M 2205/3584* (2013.01); *A61M 2205/3592* (2013.01); *A61M 2230/06* (2013.01); *A61M 2230/30* (2013.01); *A61M 2230/42* (2013.01); *A61M 2230/60* (2013.01); *A63B 21/0085* (2013.01); *A63B 2024/0093* (2013.01)

(58) Field of Classification Search
CPC .......... A61M 2230/30; A61M 2230/42; A61M 16/0683; A61M 2205/3584; A61M 2230/60; A61M 2230/06; A61M 21/02; A61M 16/20; A63B 23/18; A63B 21/0085; A63B 2024/0093
USPC ............ 128/206.11, 204.12, 204.11, 207.18, 128/206.15, 204.23
See application file for complete search history.

(56) References Cited

U.S. PATENT DOCUMENTS

| | | | |
|---|---|---|---|
| 3,869,771 A | | 3/1975 | Bollinger |
| 5,050,593 A | | 9/1991 | Poon |
| 5,598,839 A | * | 2/1997 | Niles ..................... A61M 16/08 128/205.23 |
| 2005/0165322 A1 | * | 7/2005 | Bryant .......................... 600/538 |
| 2006/0150979 A1 | | 7/2006 | Doshi et al. |
| 2007/0107737 A1 | * | 5/2007 | Landis et al. ............ 128/207.18 |
| 2007/0295338 A1 | * | 12/2007 | Loomas ................. A61M 15/08 128/207.18 |
| 2008/0035147 A1 | | 2/2008 | Kirby et al. |
| 2009/0308398 A1 | * | 12/2009 | Ferdinand et al. ...... 128/207.18 |
| 2011/0259331 A1 | * | 10/2011 | Witt .................. A61M 16/0666 128/204.18 |

FOREIGN PATENT DOCUMENTS

| | | |
|---|---|---|
| WO | 2007139890 A2 | 12/2007 |
| WO | 2008021222 A2 | 2/2008 |

* cited by examiner

SYSTEM AND METHOD FOR ENTRAINING THE BREATHING OF A SUBJECT

This application is related to U.S. patent application Ser. No. 61/161,881, entitled "SYSTEM AND METHOD FOR ADJUSTING TIDAL VOLUME OF A SELF-VENTILATING SUBJECT," and filed Mar. 20, 2009; and to U.S. patent application Ser. No. 11/836,292, entitled "SYSTEMS AND METHODS FOR CONTROLLING BREATHING RATE," and filed Aug. 9, 2007. All of these related applications are hereby incorporated into the present application in their entirety.

The invention relates to the entrainment of breathing of a subject using a respiration appliance that restricts exhalation while permitting substantially unencumbered inhalation.

Hypertension is a significant problem in nearly all western cultures and is an underlying cause for stroke and heart attack. Termed the "Silent Killer," hypertension affects approximately 1 in 4 Americans, and occurs with even higher prevalence in some European communities. Hypertension is also gaining recognition as a co-morbid factor in obstructed sleep apnea (OSA) patient populations, with recent studies indicating that as many as 80% of patients seeking treatment for OSA may unknowingly suffer from this disease.

Several conventional systems and methods exist for prompting a subject to alter respiration in a manner that will provide physiological benefits, such as lower blood pressure. However, these systems and methods generally require the use of appliances that substantially encumber the movement of users, or are not directly cuing respiration, which may reduce the effectiveness of treatment. For example, the appliances typically used to alter respiration have relatively large form factors, require a separate pressure generator for generating a pressurized flow of breathable gas, require an external power source, and/or are otherwise uncomfortable and/or inconvenient to use.

One aspect of the invention relates to a respiration appliance configured to entrain the breathing of a subject. In one embodiment, the respiration appliance comprises one or more bodies, and one or more valves. The one or more bodies are configured to enclose one or more external orifices of the airway of a subject, wherein the one or more bodies form one or more flow paths between the enclosed one or more external orifices of the airway of the subject and ambient atmosphere. The one or more valves are disposed in the one or more bodies, the one or more valves being configured to provide (i) a cumulative inhalation resistance to gas flow within the one or more flow paths formed by the one or more bodies to gas flowing from ambient atmosphere to the one or more external orifices of the airway of the subject enclosed by the one or more bodies, and (ii) a cumulative exhalation resistance to gas flow within the one or more flow paths formed by the one or more bodies to gas flowing from the one or more external orifices of the airway of the subject enclosed by the one or more bodies to ambient atmosphere. The cumulative inhalation resistance is low enough that the subject can inhale freely ambient atmosphere through the one or more bodies. The cumulative exhalation resistance is higher than the cumulative inhalation resistance, and is selected to entrain the breathing of the subject while the subject is conscious to modulate the autonomic nervous system of the subject to decrease sympathetic nerve activity and/or to reduce sympathetic/parasympathetic balance in order to provide relaxation to the subject.

Another aspect of the invention relates to a method of entraining the breathing of a subject. In one embodiment, the method comprises enclosing one or more external orifices of the airway of a subject such that one or more flow paths are formed between the enclosed one or more external orifices of the airway of the subject and ambient atmosphere; and providing, during inhalation, a cumulative inhalation resistance to gas flow within the one or more flow paths to gas flowing from ambient atmosphere to the enclosed one or more external orifices of the airway of the subject, wherein the cumulative inhalation resistance is low enough that the subject can inhale freely from ambient atmosphere through the one or more flow paths; and providing, during exhalation, a cumulative exhalation resistance to gas flow within the one or more flow paths to gas flowing from the enclosed one or more external orifices of the airway of the subject to ambient atmosphere, wherein the cumulative exhalation resistance is higher than the cumulative inhalation resistance, and is selected to entrain the breathing of the subject while the subject is conscious to modulate the autonomic nervous system of the subject to decrease sympathetic nerve activity and/or to reduce sympathetic/parasympathetic balance in order to provide relaxation to the subject.

Another aspect of the invention relates to a system configured to entrain the breathing of a subject. In one embodiment, the system comprises means for enclosing one or more external orifices of the airway of a subject such that one or more flow paths are formed between the enclosed one or more external orifices of the airway of the subject and ambient atmosphere; means for providing, during inhalation, a cumulative inhalation resistance to gas flow within the one or more flow paths to gas flowing from ambient atmosphere to the enclosed one or more external orifices of the airway of the subject, wherein the cumulative inhalation resistance is low enough that the subject can inhale freely from ambient atmosphere through the one or more flow paths; and means for providing, during exhalation, a cumulative exhalation resistance to gas flow within the one or more flow paths to gas flowing from the enclosed one or more external orifices of the airway of the subject to ambient atmosphere, wherein the cumulative exhalation resistance is higher than the cumulative inhalation resistance, and is selected to entrain the breathing of the subject while the subject is conscious to modulate the autonomic nervous system of the subject to decrease sympathetic nerve activity and/or to reduce sympathetic/parasympathetic balance in order to provide relaxation to the subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
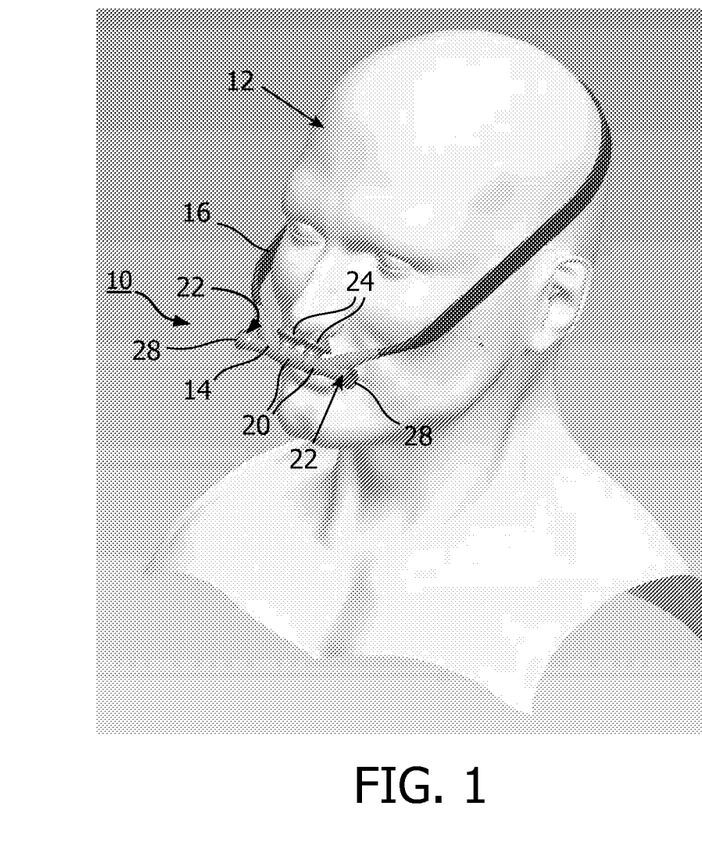
FIG. 1 illustrates a respiration appliance configured to entrain the breathing of a subject, in accordance with one or more embodiments of the invention.

FIG. 1 illustrates a respiration appliance 10 configured to entrain the breathing of a subject 12, in accordance with one or more embodiments of this disclosure. The entrainment of the breathing of subject 12 is designed to modulate the autonomic nervous system of subject 12 to decrease sympathetic nerve activity and/or to reduce sympathetic/parasympathetic balance in order to provide relaxation to subject 12. The respiration appliance 10 restricts the exhalation of subject 12 to extend the exhalation time of subject 12, which then impacts autonomic nervous system of subject 12 in the intended manner. The entrainment of the breathing of subject 12 may include impacting in a predetermined manner one or more physiological parameters of subject 12 related to respiratory rate and/or tidal volume. In one embodiment, respiration appliance 10 includes one or more bodies 14 that enclose one or more external orifices (e.g., nostrils) of the airway of subject 12, and a fastener 16.

Fastener 16 holds body 14 in place over the one or more external orifices of the airway of subject 12. In the embodiment shown in FIG. 1, fastener 16 is a single strap that loops around the head of subject 12. In one embodiment, fastener 16 includes a headgear having a different configuration for engaging the head of fastener 16 to hold body 14 in place. In one embodiment, fastener 16 includes a structure that engages the interior of the one or more openings of the airway of subject 12, and/or an adhesive that attaches to the skin of subject 12 to hold body 14 in place. In some instances (not shown), respiration appliance 10 may be implemented and/or formed integrally with an oral appliance and/or headgear that holds the lower jaw of subject 12 in a position that opens the airway of subject 12 (e.g., with the lower jaw extended forward), and/or holds the mouth of subject 12 closed to encourage breathing through the nostrils.

Figure 2:
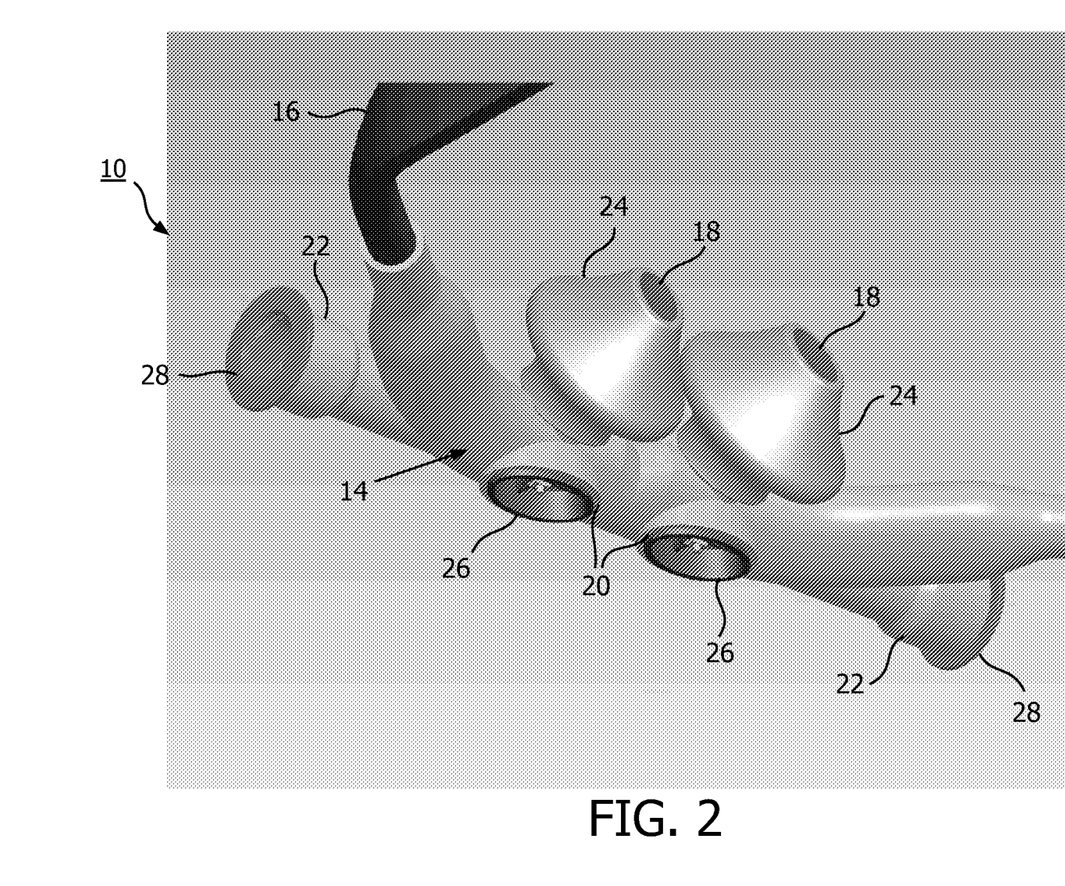
FIG. 2 illustrates a respiration appliance configured to entrain the breathing of a subject, in accordance with one or more embodiments of the invention.

FIG. 2 shows an enlarged view of body 14, according to one or more embodiments of this disclosure. As can be seen in FIG. 2, body 14 forms a plurality of openings with flow paths therebetween. In one embodiment, the interior of body 14 is hollow, and without substantial impediment to the flow of gas from any of the various openings to any of the other various openings. The plurality of openings include one or more subject interface openings 18, a set of inhalation ports 20 and a set of exhalation ports 22. The subject interface openings 18 communicate gas within the flow paths formed inside of body 14 with the airway of subject 12. As will be described further below, body 14 forms a first subset of flow paths between inhalation ports 20 and subject interface openings 18 that deliver gas from ambient atmosphere to the one or more external orifices of the airway of subject 12 during inhalation. Body 14 forms a second subset of flow paths between exhalation ports 22 and subject interface openings 18 that deliver gas from the one or more external orifices of subject 12 to ambient atmosphere during exhalation.

In one embodiment, subject interface openings 18 are formed by airway enclosing members 24. FIG. 2 depicts airway enclosing members 24 as nasal pillows that enclose the nostrils of subject 12. Airway enclosing members 24 may be selectably detachable from the rest of body 14. This will facilitate cleaning and/or replacement of airway enclosing members 24 for hygienic purposes, and/or selection of airway enclosing members 24 by subject 12 based on personal preference (e.g., from members having different sizes, different sized openings, etc.).

At the set of inhalation ports 20, respiration appliance 10 includes a set of inhalation valves 26. Inhalation valves 26 permit gas to flow relatively freely from ambient atmosphere into the flow paths formed within body 14 through inhalation ports 20, but significantly resist or seal the flow of gas from within body 14 to ambient atmosphere through inhalation ports 20. For example, inhalation valves 26 may be "one way" valves that permit gas to flow freely into body 14 from atmosphere, but block gas within body 14 from flowing to atmosphere. As such, during inhalation, the flow paths formed within body between inhalation ports 20 and subject interface openings 18 allow gas to be drawn freely from inhalation ports 20 to subject interface openings 18 and into the nostrils of subject 12. However, during exhalation, inhalation valves 26 significantly resist or seal the flow of exhaled gas from the nostrils of subject 12 to ambient atmosphere through the first subset of flow paths formed within body 14 from subject interface openings 18 to inhalation ports 20. In one embodiment, inhalation valves 26 are selectably detachable from the rest of body 14. This facilitates cleaning of valves 26 and/or body 14, and may enable valves 26 to be replaced for hygienic purposes, or if one of inhalation valves 26 stops functioning correctly.

As used herein, gas flowing "freely" from ambient atmosphere through inhalation ports 20 refers to gas flows that experience a relatively small amount of resistance such that the inhalation of this gas requires approximately the same amount of effort on the part of subject as inhalation without the respiration appliance 10. For example, in one embodiment, the resistance of inhalation valves 26 to gas flowing from ambient atmosphere into body 14 is small enough that the cumulative resistance of respiration appliance 10 to gas inhaled by subject 12 through body 14 is less than or equal to about 0.025 cm $H_2O$/LPM (at 30 LPM flow). In one embodiment, the resistance of inhalation valves 26 to gas flowing from ambient atmosphere into body 14 is small enough that the cumulative resistance of respiration appliance 10 to gas inhaled by subject 12 through body 14 is less than or equal to about 0.017 cm $H_2O$/LPM (at 30 LPM flow). Cumulative resistance is the overall resistance of respiration appliance 10 for a volume of gas flowing into a first set of openings in respiration appliance 10, through respiration appliance 10, and out of respiration appliance via a second set of openings in respiration appliance 10.

At the set of exhalation ports 22, respiration appliance 10 includes a set of exhalation valves 28. Exhalation valves 28 regulate the flow of gas between the nostrils of subject 12 and ambient atmosphere within the second subset of flow paths formed inside body 14 between subject interface openings 18 and exhalation ports 22. In particular, exhalation valves 28 provide a resistance to the flow of gas from the nostrils of subject 12 to ambient atmosphere in the second subset of flow paths during exhalation. The resistance provided by exhalation valves 28 to these flows of exhaled gas primarily characterize a cumulative resistance of respiration appliance 10 to gas being exhaled from the nostrils of subject 12. In fact, if inhalation valves 26 seal inhalation ports 20 against gas flow from within body 14 to ambient atmosphere, then the cumulative resistance of exhalation valves 28 to the flow of gas exhaled through the nostrils of subject 12 to atmosphere is the cumulative resistance of respiration appliance to gas exhaled from the nostrils of subject 12.

Figure 3:
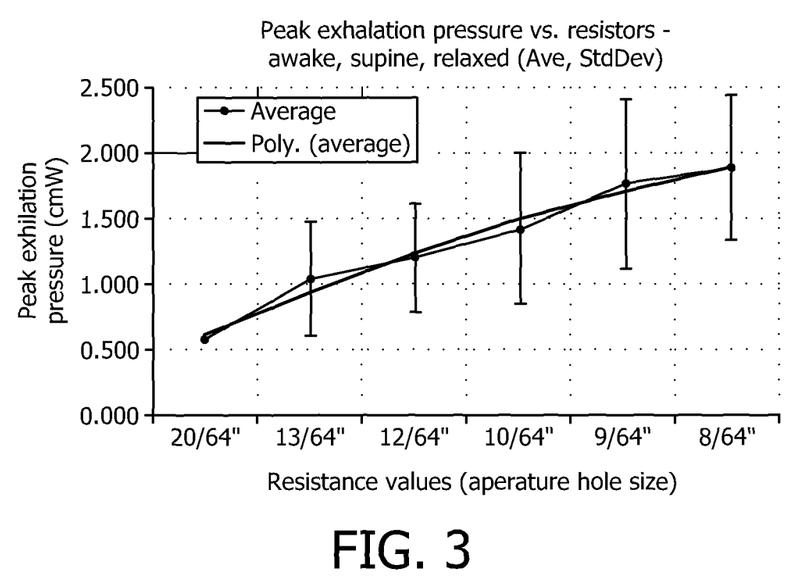
FIG. 3 is a plot illustrating the impact of a respiration appliance's cumulative resistance to exhalation has on pressure during exhalation within the respiration appliance, in accordance with one or more embodiments of the invention.

The cumulative resistance of exhalation valves 28 to the flow of exhaled gas through body 14 to ambient atmosphere reduces the flow of respiration gases (in comparison to unencumbered breathing at a given breath rate) with the same respiratory effort, and creates a pressure differential between the interior of body 14 and ambient atmosphere. Sometimes, in response to the cumulative resistance of body 14 to exhalation, subject 12 may increase respiratory effort to the extent that flow and pressure increase when breathing through body 14. By way of illustration, FIG. 3 is a plot showing the manner in which increased cumulative resistance to exhalation increases the interior pressure within body 14 (smaller aperture size=greater cumulative resistance to exhalation). This reduced flow rate of exhalation gas to ambient atmosphere, and the accompanying increase in the pressure differential between the interior of body 14 and ambient atmosphere, requires subject 12 to focus on his breathing and slow respiration to a more relaxed pace. In particular, the reduction in exhalation flow rate accomplished through the cumulative resistance of body 14 to exhalation extends the exhalation time and the overall breath period.

Figure 4:
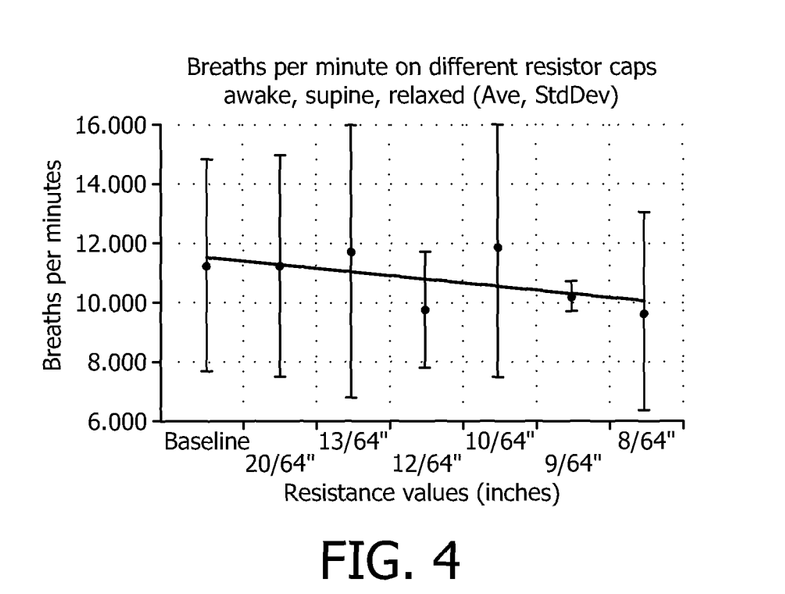
FIG. 4 is a plot illustrating the impact of a respiration appliance's cumulative resistance to exhalation has on respiratory rate by a subject using the respiration appliance, according to one or more embodiments of the invention.

At least initially, the tidal volume of respiration will tend to increase to an inflated level to compensate for the lower breath rate. Over time, as subject 12 relaxes and ventilatory demand is reduced, the tidal volume will decrease from this inflated level as autonomic nervous system arousal abates and the respiratory rate and tidal volume settle at equilibrium values. However, these equilibrium values will still be different from the unencumbered breathing of subject 12. In particular, the tidal volume will be increased with respect to unencumbered breathing, and the respiratory rate will be decreased with respect to unencumbered breathing. For example, FIG. 4 is a plot illustrating the impact that different cumulative resistances to exhalation will have on respiratory rate. In particular, FIG. 4 is a plot illustrating the impact that cumulative resistance will have on entraining the respiration of the subject while the subject is conscious. The restriction of exhalation flow by respiration appliance 10 will also tend to entrain the respiration of the subject while the subject is asleep.

In one embodiment, the user of the appliance 10 may be instructed not strain against the restricted flow during expiration. Excessive straining by the subject during exhalation may increase the pressure within respiration appliance 10 to levels that reduce the therapeutic value of respiration appliance 10, and may not enable the autonomic nervous system to be impacted in the desired manner. The instruction may be provided in the form of text provide on respiration appliance 10, one or more pictures, audible instructions, and/or other instructions.

Returning to FIG. 1, in order to provide the impact on the respiration of subject 12 described above, the exhalation valves 28 and/or inhalation valves 26 of respiration appliance 10 may be configured to provide a cumulative resistance to exhalation of between about 0.025 and about 2.0 cm-$H_2O$/LPM (at 10 LPM flow). In one embodiment, the cumulative resistance to exhalation may be between about 0.025 and about 1.0 cm-$H_2O$/LPM (at 10 LPM flow). In one embodiment, the cumulative resistance to exhalation may be between about 0.025 and about 0.45 cm-$H_2O$/LPM (at 10 LPM flow). In one embodiment, the cumulative resistance to exhalation may be between about 0.15 and about 0.45 cm-$H_2O$/LPM (at 10 LPM flow).

In one embodiment, exhalation valves 28 have a different resistance to gas flowing from ambient atmosphere to the nostrils of subject 12 through body 14 during inhalation than for gas flowing from the nostrils of subject 12 to ambient atmosphere during exhalation (e.g., exhalation valves 28 may "close" during inhalation). In one embodiment, exhalation valves 28 are fixed resistors, and have the same resistance to gas flow regardless of the direction in which the gas is flowing. In either of these embodiments, the primary inlets to body 14 for gas from ambient atmosphere during inhalation will be gas flowing through inhalation valves 26 at inhalation ports 20. Thus, the cumulative resistance to the flow of inhaled gas from ambient atmosphere to the nostrils of subject 12 through body 14 is low enough by virtue of inhalation ports 20 that subject 12 is able to inhale through body 14 freely.

As was discussed above, during exhalation by subject 12 through body 14, inhalation valves 26 block the flow of gas from body 14 to ambient atmosphere. This blockage may be accomplished by substantially sealing inhalation ports 20 and or by significantly restricting the flow of gas through inhalation ports 20. By way of example, in one embodiment, inhalation valves 26 substantially seal inhalation ports 20 (e.g., provide a resistance to permit less than or equal to about 2.5 LPM (at 5 cm $H_2O$ pressure) of gas to flow out of inhalation ports 20). As another example, in one embodiment, inhalation valves 26 provide a resistance to gas flow out of body 12 during exhalation that is high enough in comparison with the resistance of exhalation valves 28 to the flow of gas from inside body 14 to ambient atmosphere that the resistance of exhalation valves 28 controls the cumulative resistance of body 14 to exhaled gas flowing to ambient atmosphere from the airway of subject 12. For instance, with the following all being measured at about 10 LPM flow rate, the resistance of inhalation valves 26 to exhaled gas flowing from body 14 to atmosphere may be more than about 100 times smaller than the resistance of exhalation valves 28 to exhaled gas flowing from body 14 to atmosphere. In one embodiment, the resistance of inhalation valves 26 to exhaled gas flowing from body 14 to atmosphere may be more than about 50 times smaller than the resistance of exhalation valves 28 to exhaled gas flowing from body 14 to atmosphere. In one embodiment, the resistance of inhalation valves 26 to exhaled gas flowing from body 14 to atmosphere may be more than about five times smaller than the resistance of exhalation valves 28 to exhaled gas flowing from body 14 to atmosphere. In one embodiment, the resistance of inhalation valves 26 to exhaled gas flowing from body 14 to atmosphere may be smaller (e.g., more than about 2 times smaller) than the resistance of exhalation valves 28 to exhaled gas flowing from body 14 to atmosphere.

In one embodiment, the resistance of exhalation valves 28 to the flow of gas from the nostrils of subject 12 to ambient atmosphere is configurable to adjust the cumulative resistance of respiration appliance 10 to gas flowing through body 14 from subject interface openings 18 to atmosphere during exhalation. To configure the resistance of exhalation valves 28, valves 28 may be associated with one or more controls through which subject 12 or an automated control mechanism can manipulate, and/or one or more of exhalation valves 28 may be selectably detachable from exhalation ports 22 for replacement by valves having the desired resistance. In one embodiment, selectable detachment of exhalation valves 28 may facilitate cleaning of appliance 10 and/or replacement of valves that have worn out. The adjustment of resistance of exhalation valve 28 may include an adjustment to a diameter, a cross-sectional size, and/or an area of one or more openings in body 14 associated with exhalation valve 28.

In one embodiment, exhalation ports 22 may be provided with the appropriate cumulative resistance to exhaled gas without the inclusion of separate exhalation valves 28. For example, the openings in body 14 at exhalation ports 22 may be formed having a shape and/or size that resists the flow of exhaled gas at a level that provides the flow paths within body 14 with the appropriate cumulative resistance to exhaled gas. In one embodiment, port 22 may not protrude from body 14 as is illustrated in FIG. 2, but instead may be formed flush with, or more distributed over, the outer surface of body 14.

The description of the valves in body 14 that create the difference in cumulative resistance of respiration appliance 10 between inhalation gas flow and exhalation gas flow as including inhalation valves 26 and exhalation valves 28 as separate valves, or as being disposed in separate ports is not intended to be limiting. The scope of this disclosure includes embodiments of respiration appliance 10 in which the functionality of inhalation valves 26 and exhalation valves 28 is achieved by a set of valves that each provide a different resistance between inhalation and exhalation. Similarly, respiration appliance 10 may include separate types of valves that are "stacked" within common ports (e.g., one variable resistance valve and on fixed resistor) to achieve the difference in cumulative resistance of respiration appliance 10 to inhalation and exhalation.

Nevertheless, the provision of inhalation ports 20 to enable free inhalation through body 14, and exhalation ports 22 to provide a therapeutic resistance during exhalation may provide one or more enhancements over embodiments in which a single port or set of ports are provided with valves that both enable free inhalation and therapeutic resistance during exhalation through the same flow paths. For example, by implementing separate inhalation ports 20 and exhalation ports 22, respiration appliance 10 can be formed using fixed resistors for exhalation valves 28, which are simpler, more reliable, and less costly (for parts and/or during assembly of the appliances) than the types of valves that must be implemented in appliances where each opening must provide free inhalation and a therapeutic exhalation resistance. Similarly, due to the relative simplicity of the separately formed inhalation valves 26 and exhalation valves 28, the form factor of respiration appliance 10 may be enhanced. For example, valves 26 and 28, and/or appliance 10 in general may be disposed outside of the nostrils of subject 12 (as is shown in the nasal pillow configuration of FIGS. 1 and 2). In embodiments where valves 26 and 28 are formed outside of the nostrils of subject 12, some or all of the valves may have a larger cross-section than the openings of the nostrils, thereby enabling inhalation resistance of the valves 26 to be reduced. Another enhancement provided by the implementation of exhalation valves 28 in separate parts from inhalation valves 26 is that the resistance of exhalation valves 28 can be made configurable (e.g., by replacement) without disturbing the functionality or integrity of inhalation valves 26.

In one embodiment, respiration appliance 10 includes a mechanism configured to provide sensory cues to subject 12 to reduce the flow of exhalation gas from the airway of subject 12. Reducing the flow of exhalation gas from the airway of subject 12 may reduce a pressure differential between the one or more flow paths formed by the one or more bodies 14 and ambient atmosphere during exhalation. As has been discussed above, the resistance of exhalation valves 28 causes pressure to build up within body 14 and the airway of subject 12 during exhalation as exhalation gas flows out of the airway of subject 12 into body 14 faster than gas flows out of body 14 to atmosphere. This pressure causes a pressure differential between the interior of body 14 and ambient atmosphere. The pressure differential between the interior of body 14 and ambient atmosphere will tend to entrain the breathing of subject 12 to increase tidal volume and/or reduce respiratory rate (as described above). By training subject 12 to maintain the pressure different between body 14 and ambient atmosphere at a relatively low level during exhalation by voluntarily controlling the flow rate of exhalation through the airway, the subject may be trained to extend exhalation time even after respiration appliance 10 is no longer being used. This trained increase in exhalation time will be accompanied by an increase tidal volume and a reduction in respiratory rate (e.g., for the reasons described above) that extends beyond time periods during which subject 12 is using respiration appliance 10. As such, the breathing cues provided to subject 12 by the mechanism to reduce the pressure differential between the one or more flow paths formed by the one or more bodies and ambient atmosphere may have a positive impact on the breathing of subject 12 that outlasts the therapy sessions with respiration appliance 10.

In one embodiment, the mechanism configured to provide sensory cues to subject 12 to reduce the pressure differential between the one or more flow paths formed by the one or more bodies and ambient atmosphere generates the cues if the pressure differential breaches a threshold pressure differential. By way of non-limiting example, in one embodiment, the sensory cues are auditory cues. The auditory cues may be provided, for example, by one or more structures at or near exhalation valves 28 that whistle as the pressure differential between the interior of body 14 and ambient atmosphere approaches and/or breaches a threshold pressure differential. This whistle serves as an auditory cue to subject 12 to control exhalation through the airway to reduce the flow rate of exhalation into body 14.

As another non-limiting example, in one embodiment, the sensor cues are visual cues. The visual cues may be provided, for example by a movable flap (e.g., about a hinge or flexible section) disposed at or near exhalation valves 28. The flap is blown away from body 14 by the flow of gas from within body 14 to atmosphere through exhalation valves 28 if the pressure differential between the interior of body 14 and ambient atmosphere approaches and/or breaches a pressure differential threshold. The movement of the flap serves as a visual cue to subject 12 to control exhalation through the airway to reduce the flow rate of exhalation into body 14.

Figure 5:
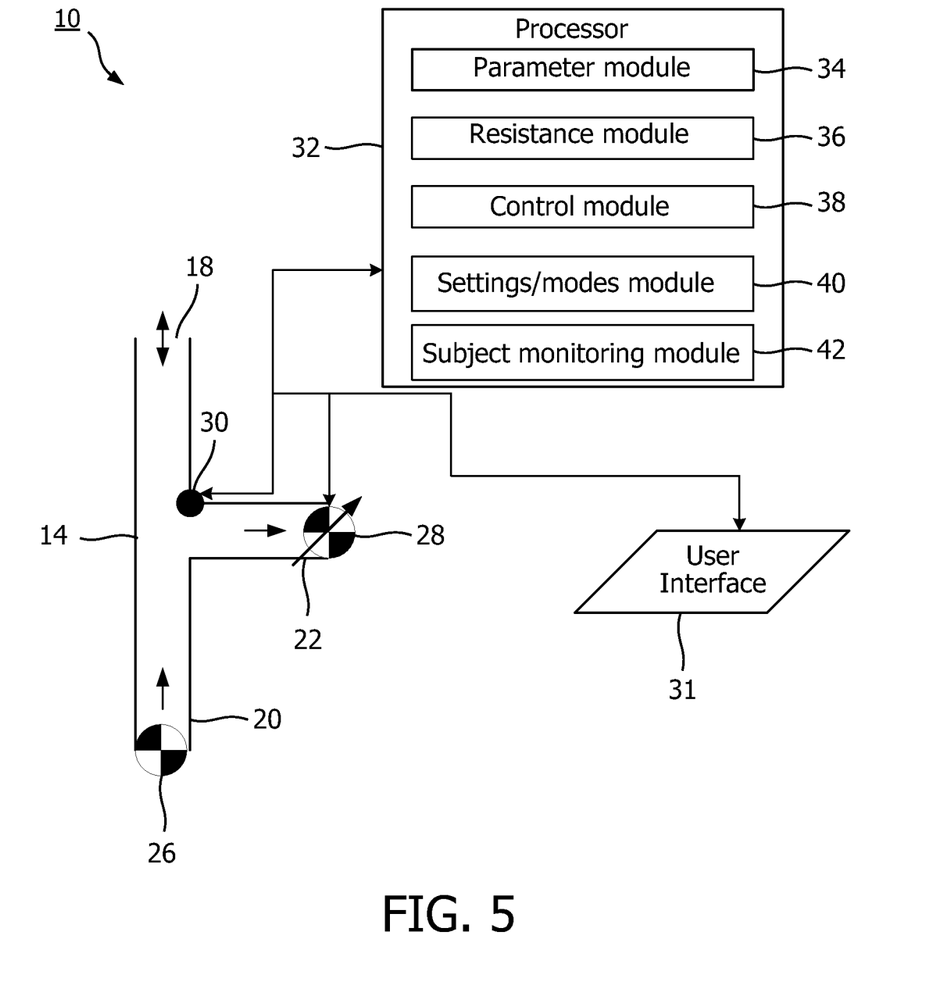
FIG. 5 illustrates a system configured to entrain the breathing of a subject, in accordance with one or more embodiments of the invention.

FIG. 5 is a block diagram of respiration appliance 10 according to one embodiment of this disclosure. In the diagram shown in FIG. 4, in addition to body 14, inhalation port 20, exhalation port 22, inhalation valve 26, and exhalation valve 28, respiration appliance 10 includes one or more sensors 30, a user interface 31, and a processor 32.

Sensors 30 are configured to generate one or more output signals that convey information related to one or more physiological parameters associated with breathing rate and/ or tidal volume of respiration. The physiological parameters may include one or more of a breathing parameter of the respiration of the subject, a cardiovascular parameter of the subject, a neurological parameter of the subject, and/or other physiological parameters impacted by and/or related to breathing rate and/or tidal volume. By way of non-limiting example, a breathing parameter associated with breathing rate and/or tidal volume of respiration may include breathing rate, tidal volume, peak flow, breath period, inhalation period, exhalation period, and/or other breathing parameters. Examples of a cardiovascular parameter associated with breathing rate and/or tidal volume of respiration may include pulse rate, pulse shape, blood pressure, blood oxygenation, and/or other cardiovascular parameters. As an example, a neurological parameter of the subject may include an EEG and/or EMG reading, and/or other neurological parameters.

In one embodiment, sensors 30 are carried on body 14. By way of non-limiting example, sensors 30 may generate one or more output signals that are indicative of one or more parameters of gas at or near the airway of the subject (e.g., within body 14). The one or more parameters may include one or more of flow rate, pressure, and/or other parameters. In one embodiment, sensors 30 include one or more sensor that is configured to generate one or more output signals indicative of one or more cardiovascular parameters of the subject. Such sensors may include, for example, a blood pressure cuff, a pressure transducer configured to detect pulse rate and/or shape, an oximeter configured to detect blood oxygenation, and/or other sensors.

User interface 31 is configured to provide an interface between appliance 10 and a user (e.g., the subject, a caregiver, a sleeping companion, etc.) through which the user may provide information to and receive information from appliance 10. This enables data, results, and/or instructions and any other communicable items, collectively referred to as "information," to be communicated between the user and processor 32. Examples of interface devices suitable for inclusion in user interface 31 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as user interface 31. For example, the present invention contemplates that user interface 31 may be integrated with a removable electronic storage interface. In this example, information may be loaded into appliance 10 from removable storage (e.g., a smart card, a flash drive, a removable disk, etc.) that enables the user(s) to customize the implementation of appliance 10. Other exemplary input devices and techniques adapted for use with appliance 10 as user interface 31 include, but are not limited to, an RS-232 port, RF link, an IR link, modem (telephone, cable or other). In short, any technique for communicating information with appliance 10 is contemplated by the present invention as user interface 31.

Processor 32 is configured to provide information processing capabilities in respiration appliance 10. As such, processor 32 may include one or more of a digital processor, an analog processor, a digital circuit designed to process information, an analog circuit designed to process information, a state machine, and/or other mechanisms for electronically processing information. Although processor 32 is shown in FIG. 5 as a single entity, this is for illustrative purposes only. In some implementations, processor 32 may include a plurality of processing units. These processing units may be physically located within the same device, or processor 32 may represent processing functionality of a plurality of devices operating in coordination.

As is shown in FIG. 5, processor 32 may be configured to execute one or more computer program modules. The one or more computer program modules may include one or more of a parameter module 34, a resistance module 36, a control module 38, a settings/modes module 40, a subject monitoring module 42, and/or other modules. Processor 32 may be configured to execute modules 34, 36, 38, 40, and/or 42 by software; hardware; firmware; some combination of software, hardware, and/or firmware; and/or other mechanisms for configuring processing capabilities on processor 32.

It should be appreciated that although modules 34, 36, 38, 40, and 42 are illustrated in FIG. 5 as being co-located within a single processing unit, in implementations in which processor 32 includes multiple processing units, one or more of modules 34, 36, 38, 40, and/or 42 may be located remotely from the other modules. The description of the functionality provided by the different modules 34, 36, 38, 40, and/or 42 described below is for illustrative purposes, and is not intended to be limiting, as any of modules 34, 36, 38, 40, and/or 42 may provide more or less functionality than is described. For example, one or more of modules 34, 36, 38, 40, and/or 42 may be eliminated, and some or all of its functionality may be provided by other ones of modules 34, 36, 38, 40, and/or 42. As another example, processor 32 may be configured to execute one or more additional modules that may perform some or all of the functionality attributed below to one of modules 34, 36, 38, 40, and/or 42.

The parameter module 34 is configured to determine information related to one or more physiological parameters related to tidal volume and/or breath rate of respiration of the subject. The parameter module 34 may determine this information based on output signals generated by sensors 30. The one or more physiological parameters may include one or more of a breathing parameter of the respiration of the subject, a cardiovascular parameter of the subject, and/or other physiological parameters impacted by and/or related to breathing rate and/or tidal volume. By way of non-limiting example, a breathing parameter associated with breathing rate and/or tidal volume of respiration may include breathing rate, tidal volume, peak flow, breath period, inhalation period, exhalation period, and/or other breathing parameters. Examples of a cardiovascular parameter associated with breathing rate and/or tidal volume of respiration may include pulse rate, pulse shape, blood pressure, blood oxygenation, and/or other cardiovascular parameters.

As is illustrated in FIG. 5, exhalation valve 28 may be configured to provide a controllable resistance to the flow of gas from the interior of body 14 to ambient atmosphere (e.g., exhaled gas). The resistance module 36 is configured to determine a cumulative resistance of respiration appliance 10 to exhalation by the subject. The cumulative resistance is determined by resistance module 36 to regulate the one or more physiological parameters related to tidal volume and/or or breath rate of respiration of the subject. For example, resistance module 36 may determine the cumulative resistance to exhalation to ensure that the one or more physiological parameters remain at or near a target value. The target value may be a therapeutically beneficial level for the one or more physiological parameters.

In one embodiment, resistance module 36 determines the cumulative resistance of respiration appliance 10 to exhalation by the subject in a feedback manner. In this embodiment, resistance module 36 monitors determinations of information related to the one or more physiological parameter related to tidal volume and/or breath rate, and adjusts the cumulative resistance to exhalation to maintain the one or more physiological parameters at or near the target value(s).

In one embodiment, resistance module 36 is configured to ramp the cumulative resistance to exhalation gradually over time such that the value of the one or more physiological parameters related to tidal volume and/or breathing rate are guided gradually to the target value(s). This may enhance the comfort of respiration appliance 10 to the subject upon initiating a session of treatment, which may tend to increase subject compliance. In one embodiment, the ramping of the cumulative resistance is performed by resistance module 36 according to a ramping algorithm. In one embodiment, the rate (and/or increments) at which the cumulative resistance is ramped may be determined based on response of the one or more physiological parameters to the cumulative resistance.

Control module 38 is configured to control the resistance of exhalation valve 28 to this flow of gas. More particularly, control module 36 controls the resistance of exhalation valve 28 to the flow of gas from the interior of body 14 to provide body 14 with the cumulative resistance to exhalation determined by resistance module 36. Controlling the resistance of exhalation valve 28 may include controlling a single valve, or a plurality of valves cooperating to provide the functionality attributed herein to exhalation valve 28.

The settings/modes module 40 is configured to control the mode that respiration appliance 10 is operating in, and/or the settings of respiration appliance 10. The modes of operation of respiration appliance 10 may include a plurality of different modes. The plurality of different modes may include different modes for breathing entrainment and for airway support. This would enable the subject to use respiration appliance 10 during the day (or even at night) for breathing entrainment to impact the one or more physiological parameters related to tidal volume and/or respiratory rate, and use respiration appliance 10 at bedtime to provide airway support as treatment for sleep disordered breathing. The settings/modes module 40 may automatically switch between these modes (e.g., based on a predetermined timing, an ambient radiation level, a motion sensor, and/or other sensors or detectors), and/or settings/modes module 40 may switch between these modes based on input for the subject (e.g., via user interface 31).

The settings of respiration appliance 10 include settings that control the manner in which the cumulative resistance of body 14 to exhalation is adjusted. For example, the settings may include a setting that dictates the target value of the one or more physiological parameters, a setting that dictates whether the cumulative resistance of body 14 to exhalation is ramped up upon commencement of use, a setting that dictates the rate at which the cumulative resistance of body 14 to exhalation is ramped, inhalation resistance, maximum or minimum pressure, pressure profile over the respiratory cycle, a defined control function that responds to sensory parameters (e.g., systematically increasing resistance to reach a subject's goal of reduced blood pressure or sympathetic nervous activity, etc.), and/or other settings.

The subject monitoring module 42 is configured to monitor the subject receiving treatment from respiration appliance 10. This includes monitoring the amount of therapy received by the subject from respiration appliance 10. By way of non-limiting example, the amount of therapy received by the subject may be quantified in terms of the amount of time respiration appliance 10 is used, the impact on the one or more physiological parameters associated with tidal volume and/or respiratory rate, the amount of time for which the one or more physiological parameters satisfy the target value, and/or other mechanisms quantifying the amount of therapy received by the subject.

It will be appreciated that at least some of the features and functionality attributed to respiration appliance 10 in FIG. 5 may be implemented in an embodiment not including an electronic processor such as processor 32. By way of non-limiting example, respiration appliance 10 may include a plurality of modes of operation that are selected by a user manually by a non-electronic interface provided on respiration appliance 10. For instance, user interface 31 may include a dial or knob that mechanically adjusts the resistance of exhalation valve 28. The dial or knob may indicate a plurality of positions that correspond to different settings (e.g., breath entrainment, pressure support, etc.). Similarly, one or more settings of respiration appliance 10 may be manually adjusted by the subject. For instance, user interface 31 may include a knob, a dial, lever, a switch, and/or another interface that mechanically adjusts the resistance of exhalation valve 28 between resistance settings.

As another example, the gradual ramping of resistance described above with respect to exhalation valve 28 could be accomplished by a mechanical mechanism for gradually restricting gas flow through valve 28 (e.g., by gradually restricting the diameter and/or cross-section of one or more openings formed at valve 28). For instance, a memory polymer may be inserted in one or more openings formed at valve 28. The memory polymer may contract after being enlarged (e.g., by an inserted plug). Valve 28 may include a memory metal/polymer/nano-structure that pulls or pushes a membrane (or membranes) to close an opening associated with valve 28 after the membrane/memory structure is placed in an initial open position by a reset mechanism. Valve 28 may include a spring-based clock-like mechanism that is released by breath pressure pressing against a membrane (or membranes) to slowly close an opening at valve 28. Valve 28 may include a rocking-ratchet clock mechanism (fixed or pre-programmed time actuated) to slowly close a valve opening. Other mechanisms for slowly closing a valve opening associated with valve 28 to ramp resistance are also contemplated.

In one embodiment, the mechanical mechanism included in valve 28 to slowly ramp resistance over time without control from an electrical processor may include an activation control. The activation control may be activated by the subject or by another individual in the vicinity of subject during sleep (e.g., a spouse, a parent, a caregiver, etc.) as needed.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A respiration appliance configured to entrain the breathing of a subject, the respiration appliance comprising:
   a body configured to enclose two external orifices of an airway of the subject, wherein the body forms one or more flow paths between the two enclosed external orifices of the airway of the subject and ambient atmosphere, the one or more flow paths comprising a first subset of flow paths between two inhalation ports formed by the body and the two external orifices, and a second subset of flow paths between two exhalation ports formed by the body and the two external orifices, the two inhalation ports being located remotely from the two exhalation ports, the two exhalation ports being located remotely from each other;

one or more valves disposed in the body, the one or more valves comprising two inhalation valves individually coupled with the two inhalation ports and two exhalation valves individually coupled with the two exhalation ports, the one or more valves being configured to provide (i) a cumulative inhalation resistance to gas flow within the one or more flow paths to gas flowing from ambient atmosphere to the two external orifices of the airway of the subject, and (ii) a cumulative exhalation resistance to gas flow within the one or more flow paths to gas flowing from the two external orifices of the airway of the subject to ambient atmosphere, wherein the cumulative inhalation resistance is low enough that the subject can inhale freely from ambient atmosphere through the body, and wherein the cumulative exhalation resistance is higher than the cumulative inhalation resistance, and is selected to entrain the breathing of the subject while the subject is conscious to modulate the autonomic nervous system of the subject to decrease sympathetic nerve activity and/or to reduce sympathetic/parasympathetic balance in order to provide relaxation to the subject;

a movable flap disposed at or near one of the exhalation valves, wherein the movable flap is configured to be moved away from the body in response to a pressure differential between the one or more flow paths formed by the body and ambient atmosphere breaching a threshold pressure differential, and wherein the movable flap moving away from the body is configured to prompt the subject to alter their breathing;

one or more sensors configured to generate one or more output signals conveying information related to a physiological parameter; and a processor in operative communication with the one or more sensors, the processor being configured to automatically adjust operation of the two exhalation valves to control the cumulative exhalation resistance based on the one or more output signals generated by the one or more sensors to modulate the physiological parameter.

2. The respiration appliance of claim 1, wherein the entrainment of the breathing of the subject modulates in a predetermined manner a physiological parameter associated with a breathing rate and/or a tidal volume of respiration.

3. The respiration appliance of claim 1, wherein the automatic adjustment of the operation of the two exhalation valves configured to control the cumulative exhalation resistance comprises controlling the two exhalation valves to ramp the cumulative resistance to exhalation gradually over time to modulate the physiological parameter until a target physiological parameter is reached.

4. The respiration appliance of claim 1, wherein the physiological parameter comprises blood pressure.

5. The system of claim 1 wherein:
a first one of the two enclosed external orifices and a first one of the two inhalation ports are located along a first axis of the body;

a second one of the two enclosed external orifices and a second one of the two inhalation ports are located along a second axis of the body;

the two exhalation ports are located along a third axis of the body at opposite ends of the body;

the first axis and the second axis are substantially parallel; and the third axis is substantially perpendicular to the first axis and the second axis.

6. A method of entraining the breathing of a subject with a respiration appliance, the respiration appliance comprising a body, a movable flap, one or more sensors, and one or more physical computer processors, the method comprising:

enclosing two external orifices of an airway of the subject with the body such that one or more flow paths are formed between the two enclosed external orifices of the airway of the subject and ambient atmosphere, the one or more flow paths comprising a first subset of flow paths between two inhalation ports formed by the body and the two external orifices, and a second subset of flow paths between two exhalation ports formed by the body and the two external orifices, the two inhalation ports being located remotely from the two exhalation ports, the two exhalation ports being located remotely from each other;

providing, during inhalation with one or more valves disposed in the body, a cumulative inhalation resistance to gas flow within the one or more flow paths to gas flowing from ambient atmosphere to the two enclosed external orifices of the airway of the subject, wherein the cumulative inhalation resistance is low enough that the subject can inhale freely from ambient atmosphere through the one or more flow paths, and wherein the one or more valves comprise two inhalation valves individually coupled with the two inhalation ports and two exhalation valves individually coupled with the two exhalation ports; and providing, during exhalation with the two inhalation valves and the two exhalation valves, a cumulative exhalation resistance to gas flow within the one or more flow paths to gas flowing from the two enclosed external orifices of the airway of the subject to ambient atmosphere, wherein the cumulative exhalation resistance is higher than the cumulative inhalation resistance, and is selected to entrain the breathing of the subject while the subject is conscious to modulate the autonomic nervous system of the subject to decrease sympathetic nerve activity and/or to reduce sympathetic/parasympathetic balance in order to provide relaxation to the subject;

disposing the movable flap at or near one of the exhalation valves, wherein the movable flap is moved away from the body due to a pressure differential between the one or more flow paths formed by the means for enclosing and ambient atmosphere breaching a threshold pressure differential, and wherein the movable flap moving away from the body is configured to prompt the subject to alter their breathing;

generating, with the one or more sensors, one or more output signals conveying information related to a physiological parameter; and adjusting, with the one or more physical computer processors, operation of the two exhalation valves to control the cumulative exhalation resistance automatically based on the one or more output signals generated by the one or more sensors to modulate the physiological parameter.

7. The method of claim 6, wherein the entrainment of the breathing of the subject modulates in a predetermined manner a physiological parameter associated with a breathing rate and/or a tidal volume of respiration.

8. The method of claim 6, wherein the adjusting operation of the two exhalation valves to control the cumulative exhalation resistance automatically comprises controlling the two exhalation valves to ramp the cumulative resistance to exhalation gradually over time to modulate the physiological parameter until a target physiological parameter is reached.

9. The method of claim 6, wherein the physiological parameter comprises blood pressure.

10. The method of claim 6 wherein:
   a first one of the two enclosed external orifices and a first one of the two inhalation ports are located along a first axis of the body;
   a second one of the two enclosed external orifices and a second one of the two inhalation ports are located along a second axis of the body;
   the two exhalation ports are located along a third axis of the body at opposite ends of the body;
   the first axis and the second axis are substantially parallel; and
   the third axis is substantially perpendicular to the first axis and the second axis.

11. A system configured to entrain the breathing of a subject, the system comprising:
   means for enclosing two external orifices of an airway of the subject such that one or more flow paths are formed between the two enclosed external orifices of the airway of the subject and ambient atmosphere, the one or more flow paths comprising a first subset of flow paths between two inhalation ports formed by the means for enclosing and the two external orifices, and a second subset of flow paths between two exhalation ports formed by the means for enclosing and the two external orifices, the two inhalation ports being located remotely from the two exhalation ports, the two exhalation ports being located remotely from each other;
   means for providing, during inhalation with one or more valves disposed in the means for enclosing, a cumulative inhalation resistance to gas flow within the one or more flow paths to gas flowing from ambient atmosphere to the two enclosed external orifices of the airway of the subject, wherein the cumulative inhalation resistance is low enough that the subject can inhale freely from ambient atmosphere through the one or more flow paths, and wherein the one or more valves comprise two inhalation valves individually coupled with the two inhalation ports and two exhalation valves individually coupled with the two exhalation ports; and
   means for providing, during exhalation with the two inhalation valves and the two exhalation valves, a cumulative exhalation resistance to gas flow within the one or more flow paths to gas flowing from the two enclosed external orifices of the airway of the subject to ambient atmosphere, wherein the cumulative exhalation resistance is higher than the cumulative inhalation resistance, and is selected to entrain the breathing of the subject while the subject is conscious to modulate the autonomic nervous system of the subject to decrease sympathetic nerve activity and/or to reduce sympathetic/parasympathetic balance in order to provide relaxation to the subject;
   movable flap means disposed at or near one of the exhalation valves, wherein the movable flap means is configured to be moved away from the means for enclosing due to a pressure differential between the one or more flow paths formed by the means for enclosing and ambient atmosphere breaching a threshold pressure differential, and wherein the movable flap means moving away from the means for enclosing is configured to prompt the subject to alter their breathing;
   means for generating one or more output signals conveying information related to a physiological parameter; and
   means for adjusting the operation of the two exhalation valves to control the cumulative exhalation resistance automatically based on the generated one or more output signals to modulate the physiological parameter.

12. The system of claim 11, wherein the entrainment of the breathing of the subject modulates in a predetermined manner a physiological parameter associated with a breathing rate and/or a tidal volume of respiration.

13. The system of claim 11, wherein the means for adjusting the two exhalation valves to control the cumulative exhalation resistance automatically comprises controlling the two exhalation valves to ramp the cumulative resistance to exhalation gradually over time to modulate the physiological parameter until a target physiological parameter is reached.

14. The system of claim 11, wherein the physiological parameter comprises blood pressure.

15. The system of claim 11 wherein:
   a first one of the two enclosed external orifices and a first one of the two inhalation ports are located along a first axis of the means for enclosing;
   a second one of the two enclosed external orifices and a second one of the two inhalation ports are located along a second axis of the means for enclosing;
   the two exhalation ports are located along a third axis of the means for enclosing at opposite ends of the means for enclosing;
   the first axis and the second axis are substantially parallel; and
   the third axis is substantially perpendicular to the first axis and the second axis.

* * * * *